(12) United States Patent
Vinson

(10) Patent No.: US 10,413,380 B2
(45) Date of Patent: Sep. 17, 2019

(54) ILLUMINATED CATHETERIZATION DEVICE

(71) Applicant: Anthony Vinson, Fallbrook, CA (US)

(72) Inventor: Anthony Vinson, Fallbrook, CA (US)

( * ) Notice: Subject to any disclaimer, the term of this patent is extended or adjusted under 35 U.S.C. 154(b) by 963 days.

(21) Appl. No.: 14/925,852

(22) Filed: Oct. 28, 2015

(65) Prior Publication Data

US 2016/0113718 A1 Apr. 28, 2016

Related U.S. Application Data

(60) Provisional application No. 62/069,757, filed on Oct. 28, 2014.

(51) Int. Cl.
*A61B 90/30* (2016.01)
*A61B 90/10* (2016.01)
*A61B 90/11* (2016.01)
*A61M 25/01* (2006.01)
*A61B 90/00* (2016.01)

(52) U.S. Cl.
CPC .............. *A61B 90/10* (2016.02); *A61B 90/11* (2016.02); *A61B 90/30* (2016.02); *A61B 90/36* (2016.02); *A61M 25/0105* (2013.01); *A61B 2090/309* (2016.02); *A61M 2025/0166* (2013.01)

(58) Field of Classification Search
CPC .... A61M 25/0105; A61B 90/36; A61B 90/11; A61B 90/30
USPC .......................................... 600/249, 461, 478
See application file for complete search history.

(56) References Cited

U.S. PATENT DOCUMENTS

| | | | |
|---|---|---|---|
| 5,718,666 A * | 2/1998 | Alarcon | A61B 5/0059 362/551 |
| 6,286,514 B1 * | 9/2001 | Lemelson | A61B 17/320758 128/899 |
| 7,917,193 B2 * | 3/2011 | Crane | A61B 5/06 600/473 |
| 2003/0187360 A1 * | 10/2003 | Waner | A61B 5/0059 600/478 |

* cited by examiner

*Primary Examiner* — Si Ming Ku
(74) *Attorney, Agent, or Firm* — Donn K. Harms

(57) ABSTRACT

An illuminated catheter adapted for engagement on an introducer is provided which employs a lighting component to communicate light to and through a catheter. The illumination emanating from the catheter during insertion into a patient can illuminate the insertion site and once inserted provide the user illumination which is visually discernible to determine communication of the distal end of the catheter to and into a blood vessel.

20 Claims, 2 Drawing Sheets

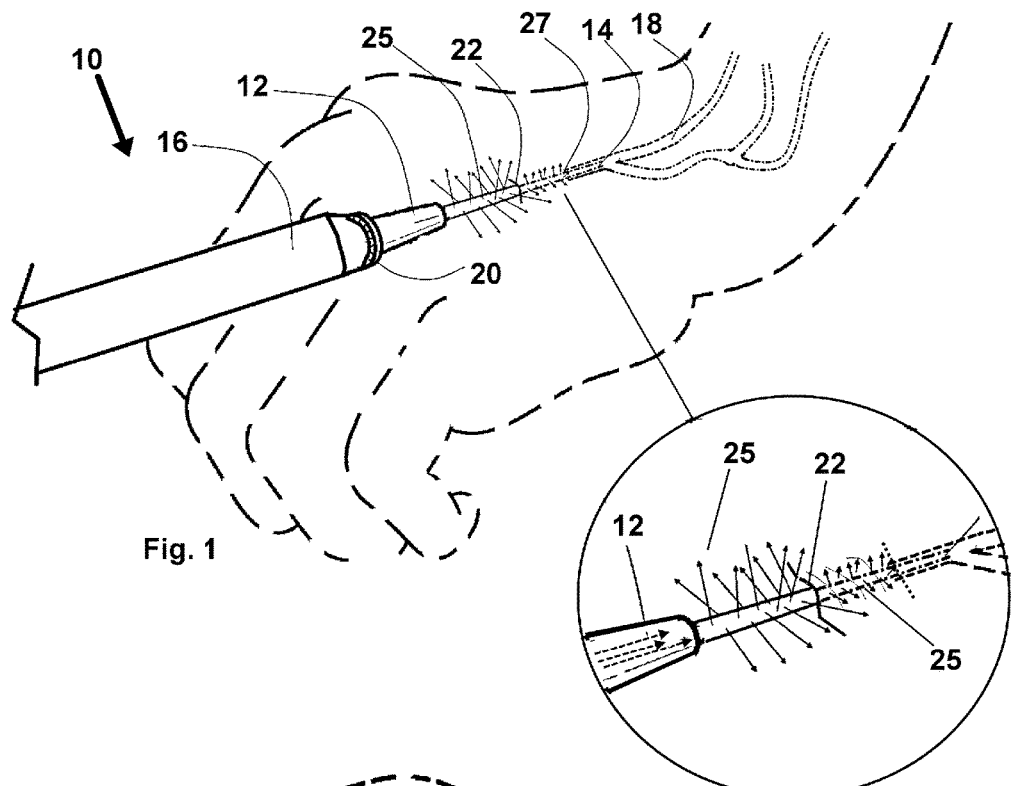
Fig. 1
Fig. 2
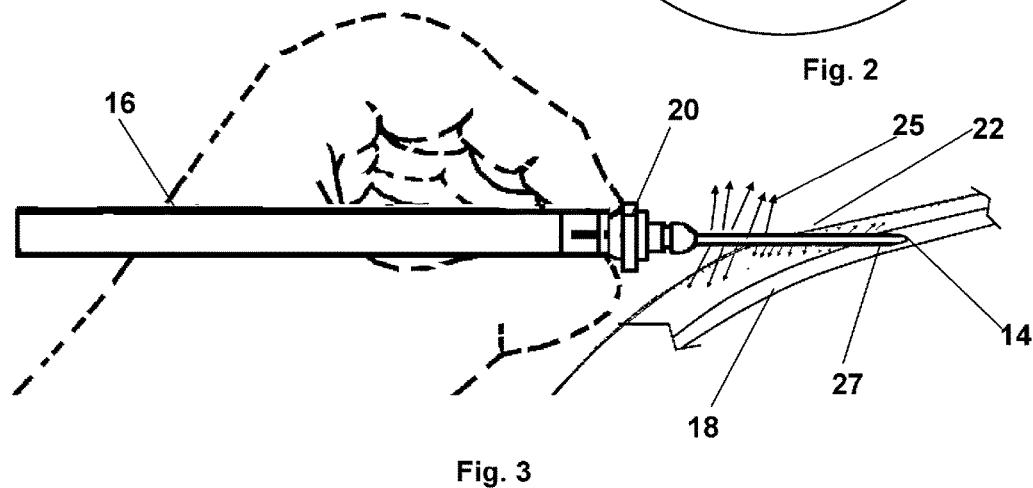
Fig. 3

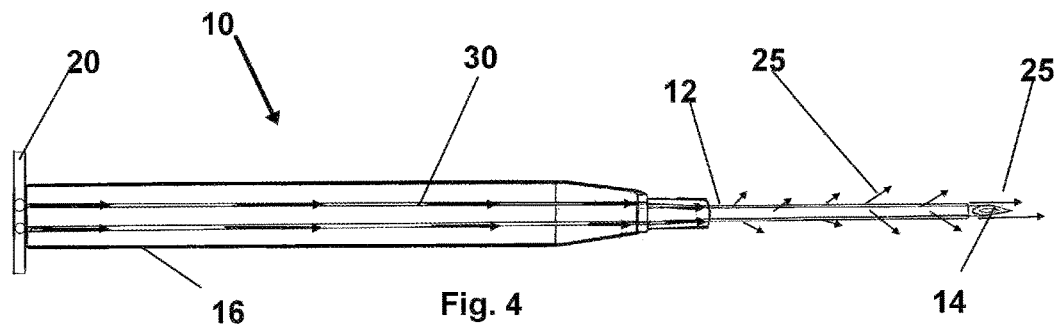
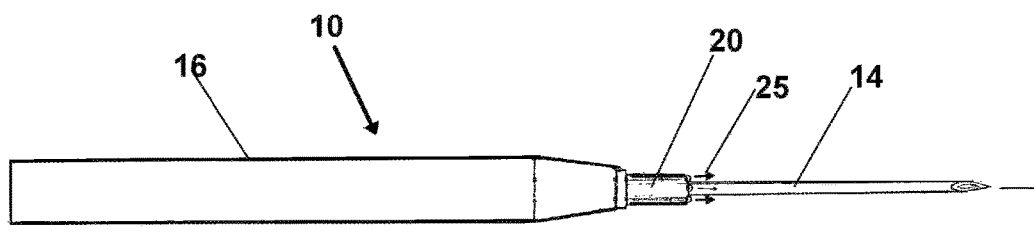
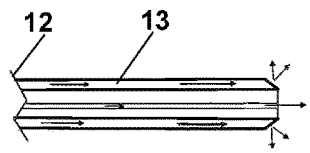
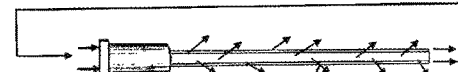
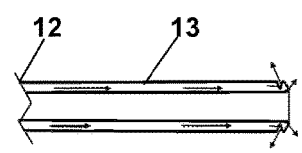
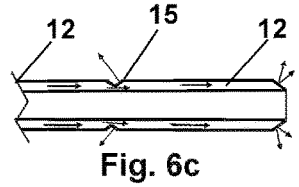
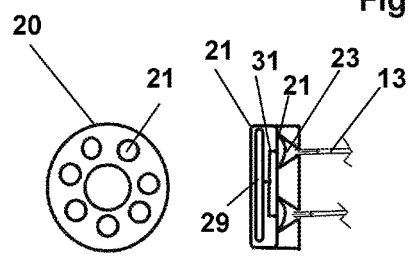
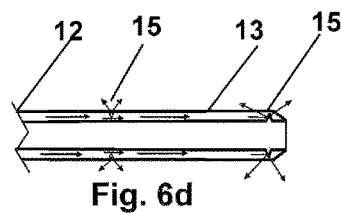

ILLUMINATED CATHETERIZATION DEVICE

This application is a U.S. Nonprovisional Patent Application which claims benefit of U.S. Provisional Patent Application Ser. No. 62/069,757 filed on Oct. 28, 2014, which is incorporated herein in its entirety by this reference thereto.

FIELD OF THE INVENTION

The present device relates to catheter insertion devices which are employed for the placement of a catheter into the vein or artery of a patient. More particularly, the disclosed device relates to an implanted catheter component which communicates to the skin prior to insertion and through the skin from the catheter being inserted. In this fashion both the chosen insertion site and the translation progress of the catheter into a vein during placement thereof may be observed from outside the body of the patient.

BACKGROUND OF THE INVENTION

Intravenous catheters for the infusion of fluids and medicine into the peripheral veins of a patient are one of the most common devices used in the medical profession where patients require medical care or surgery. Health care professionals are as such, frequently required to place the distal end of such a catheter within the confines of a vein or artery of the patient. Properly positioned, such a catheter allows the health care provider to communicate blood, drugs, plasma, and other fluids into the circulatory system of a patient directly yielding immediate results. It also provides a direct venous access line for hospital personnel, to allow for immediate intravenous care upon arrival at a hospital.

However, this procedure when performed by unskilled hands can be painful and cause trauma to the patient. Some medical professionals require years to learn to properly place the flexible catheter in a patent, while imparting minimal pain and discomfort to the patient. In cases where the patient may be chilled or otherwise have small venous cavities, or an adult with collapsed or impaired veins or arteries, proper placement of the catheter can be exceptionally hard to accomplish, especially if the medical professional is less than adept at the procedure. During insertion of a catheter into a patient's blood vessel, a catheter insertion device commonly known as an introducer is conventionally employed. Such devices conventionally are equipped with a hollow needle which is inserted to puncture both the skin of the patient, and if properly placed, puncture only one wall of the intended blood vessel. The catheter device rides on the exterior of the rigid needle of the introducer.

During catheter placement with the introducer, once the needle punctures the skin, it must then be blindly, but successfully, communicated through underlying tissue, with minimal damage thereto, and puncture one wall of the intended blood vessel without extending too far that the opposing side of the blood vessel is punctured. With the distal end of the needle properly placed, blood travels through the length of the hollow needle and exits into a viewable flash chamber of the introducer, in a surge called a flashback.

In typical catheter insertion assemblies, for use by emergency personnel the user removes and disposes the contaminated needle after puncturing one wall of the intended blood vessel and a subsequent slight translation of the distal end of the catheter prior to needle removal.

However, emergency responders and care takers can be required to achieve a proper catheter placement in conditions far removed from the warm and well lighted hospital or doctors office. On a dark roadway or in other less than desirable conditions, the catheter still must be inserted and properly placed in the vein of the patient irrespective of lighting conditions, weather, and temperature.

One mode for emergency responders to deal with such challenging conditions is to hold a small flashlight between their teeth. Light from this flashlight is projected on the intended insertion target on the arm, hand or leg, whereafter the medical professional or emergency responder will pick a position on the skin of the patient for needle puncture and then attempt to blindly find the vein of choice for the puncture by the needle and subsequent catheter insertion prior to needle removal.

As can be discerned, it can be very hard for the medical professional or emergency responder to illuminate the puncture site and then to insert a needle and actually find the blood vessel hidden from sight below the skin of the patient. Further, even if they navigate by touch or intuition to a blood vessel, it can be very hard to know one side has been punctured unless the blood flows sufficiently fast to the flash chamber of the introducer to inform the medical professional they have punctured the blood vessel and have blood flow. Many times, in the haste that emergencies require, both sides of the intended vessel can be punctured.

As such, there is an unmet need for an intravascular catheter insertion device and method, which will provide illumination of the intended puncture site, prior to insertion. Such a device and method should also provide the user with a viewable position of the needle, and the surrounding catheter once translated under the skin, to ascertain the progress toward a blood vessel. Further, such a device should visually inform the user they have indeed punctured a blood vessel immediately upon such an occurrence to provide a faster or at least a concurrent notice to the user of proper needle insertion through only one side of a blood vessel. Finally, such a device and method should be low in cost to encourage use and be easily adapted into the employed standards for catheters and introducers used widely in the medical field.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

OBJECTS OF THE INVENTION

It is an object of the present invention to provide an intravenous catheter insertion device and method which provides illumination of the skin puncture site during use.

It is an additional object of this invention to provide the user with a viewable progress of the catheter and needle translation once under the skin of the patient and out of direct view of the user.

Still further, it is an object of the invention herein to provide visual feedback and confirmation of the puncture of an intended blood vessel under the skin of the patient, in real time in a readily discernable fashion using projected light from the insertable catheter.

These and other objects, features, and advantages of the present invention, as well as the advantages thereof, over existing prior art, which will become apparent from the description to follow, are accomplished by the improvements described in this specification and hereinafter described in the following detailed description which fully discloses the invention, but should not be considered as placing limitations thereon.

SUMMARY OF THE INVENTION

In accordance with the purposes of the present invention, as embodied and broadly described herein, the present invention provides a catheter insertion device and method which is configured to provide self-illumination of the catheter itself, in a manner which projects light therefrom onto the skin and proposed insertion site of the needle of the introducer. Employing one or a plurality of light sources, in operative communication with the hollow tubing defining the catheter to render it a fiberoptic illumination component, the device is easily included into the construction of conventional introducers or can be added thereto with annular light projection components adapted to project light to and through the catheter wall.

During insertion of a catheter with an insertion set, the needle, extends through a needle hub, and thereafter through the passage of a catheter which surrounds all but a distal point on the needle. Using the device and method herein, the catheter material is illuminated through the communication of light thereto from LEDs or another low power means for illumination which may be linearly directed into the proximal end of the catheter which is mounted at the communication of the proximal end of the needle with the introducer.

Illumination may be provided by engagement of a plurality of LEDs to the front or rear of the introducer housing in a fashion which will communicate light emitted therefrom, into the sidewall defining the catheter surrounding the needle. Because maximum light transmission though the skin and flesh underneath is desirable in order to track the needle position, direction and translation progress during insertion, light which can be seen through the skin is the most desirable wavelength to employ which currently is in the 650 to 1350 nm wavelengths with current favored wavelengths being between 700 to 900 nm which is a range found to travel well through skin and flesh such that the illuminated catheter surrounding the needle of the introducer may be tracked once inserted under the skin.

During translation of the needle surrounded by the illuminated catheter under the skin of the patient, to complete the insertion by puncturing one wall of a blood vessel, the user can view the distal end of the illuminated catheter and ascertain the position of the needle projecting therefrom. Upon puncturing a blood vessel, such can be ascertained once the user views the distal end of the illuminated catheter dim, or disappear which is a discernable viewable signal that the distal end of the catheter and the needle, have translated through the wall of a blood vessel and into position.

With respect to the above description, before explaining at least one preferred embodiment of the herein disclosed catheter insertion illumination system invention in detail, it is to be understood that the invention is not limited in its application to the details of construction and to the arrangement of the components in the following description or illustrated in the drawings. The device herein described and disclosed in the various modes and combinations is also capable of other embodiments and of being practiced and carried out in various ways which will be obvious to those skilled in the art. Any such alternative configuration as would occur to those skilled in the art is considered within the scope of this patent. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other illuminated catheter insertion devices and blood testing equipment for carrying out the several purposes of the present disclosed device. It is important, therefore, that the claims be regarded as including such equivalent construction and methodology insofar as they do not depart from the spirit and scope of the present invention.

BRIEF DESCRIPTION OF DRAWING FIGURES

The accompanying drawings, which are incorporated herein and form a part of the specification, illustrate some, but not the only nor exclusive examples of embodiments and/or features of the disclosed device. It is intended that the embodiments and figures disclosed herein are to be considered illustrative of the invention herein, rather than limiting in any fashion.

In the drawings:

FIG. 1 depicts an isometric view of the over the needle catheter device herein in an as-used positioning puncturing a patient's skin and showing the visually discernible light emitted from the illumination shown as projecting arrows from the catheter in the drawing.

FIG. 2 is an enlargement of a portion of FIG. 1 showing the darkening of light emissions from the distal end of the catheter under the skin, once it punctures the blood vessel of the patient, thereby providing a signal to the user of successful positioning within a lumen or vessel.

FIG. 3 shows a side view of the device in use in a similar fashion to that of FIG. 1, and showing the brightness of visually discernible light emanating from the catheter and the brighter proximal end and dimmer distal end, depending on its position above or under the patient's skin.

FIG. 4 displays one mode of communication of the noted light or illumination to the catheter, shown engaged upon an introducer having an engaged LED or other discernible light generating device which is communicated through fiberoptic channels to the proximal end of the catheter which is adapted to channel the light through and from the sidewall defining the catheter surrounding a needle.

FIG. 5 shows another mode of provision of illumination for communication of such into a catheter engaged with an introducer showing the catheter disengaged from the needle.

FIGS. 6 A-D depict examples of some modes of the catheter herein wherein one or a plurality of projecting lenses are formed on or into the polymeric material forming the catheter, to better project radially therefrom and through tissue and skin to render the catheter and its location discernable from outside the body of the patient.

FIG. 7a depicts an LED light generating component formed in an annular array of LED's for projecting light into the modes of the device herein described.

FIG. 7b depicts a sectional view of a light generating component such as in FIG. 7a and shows the onboard battery and internal circuitry to communicate electric power to the LEDs and also showing a focusing lens which channels the light generated by the LEDs into a sidewall of either the catheter or flash chamber.

DETAILED DESCRIPTION OF THE INVENTION

Now referring to drawings in FIGS. 1-7, wherein similar components are identified by like reference numerals, there is seen in FIGS. 1-2, the light emitting catheter device 10 depicted in an as-used configuration during insertion of an intravenous catheter 12 into a blood vessel of a patient. The catheter 10 component of the device 10 is shown in operative positioning surrounding a needle 14 of an introducer 16. Such introducers 16 are conventionally employed for catheter 10 insertion and positioning and have an internal flash chamber. Blood entering this flash chamber is visible during the procedure and the sight of such alerts the user of success in positioning the distal end of the needle 14, within the confines of a blood vessel 18. Of course the distal end of the needle 14 itself cannot be seen by the user in conventionally employed introducers, which is a significant shortfall in using such during the entire insertion process.

As shown in FIG. 1, a light generating component 20 can employ LEDs 21 (FIG. 7a), other light emitters such as bulbs. LED's are a particular favorite herein as they have low electric power requirements and can be chosen to project in a light spectrum most likely to transmit through skin and tissue. The light generated by the light generating component 20 and communicated to and through the catheter 12 herein, allows the user to track the progress of the catheter 12 and needle 14 projecting therefrom, once the skin is punctured at an insertion site 22 on the patient. Choosing a light spectrum adapted to communicate through tissue will enhance discernible light for the user. Still further, prior to insertion, the user can employ the light emitted from the catheter 12 which is transmitted thereto by the light generating component 20, to illuminate the skin of the patient to choose the desired insertion site 22. Such would be most helpful in a dark environment such as for an emergency responder at night outdoors.

In a preferred mode of the device 10 the light generating component 20 projects light to be communicated to and from the catheter 12 a wavelength between 650 to 1350 nm with a current most preferred wavelength between 700 to 900 nm which has been found in experimentation, to better transmit through the skin and underlying flesh to provide the user the best viewable illumination or light emanation allowing the user to see a position the distal end and a central portion of the elongated catheter 12 once communicated through the insertion site 22 where the distal end is under the skin of the patient.

As can be seen in FIG. 2, the arrows signify transmitted light 25 emanating from the catheter 12. The discernible light can be seen by a user communicating in three pathways in three differing intensities including light emanating directly from the catheter 12 unimpeded, or in a second pathway where the light communicates through the skin, or in a third pathway where the visually discernible light must communicate through the wall of a blood vessel as well as the skin of a patient.

As depicted in FIG. 2, the length of the arrows is representative of the relative brightness of the communicated light 25 through these three differing light paths. The area of the catheter 12 exterior to the puncture at the insertion site 22 communicates to the eyes of the user along the first pathway which is brighter and will also illuminate the skin of the patient prior to the insertion to help pick a target. The arrows showing light emanating from the catheter which are progressively shorter, depict the light discernible by the user along the other two pathways which the device 10 in the as-used position.

In FIG. 2 can also be seen that the catheter 12 illuminated beneath the skin of the patient along a mid portion thereof between the distal end 27 and first end adjacent the introducer 16, can be seen as dimmer that light emitting from the first end. This light emanating from the catheter 12 prior to puncturing a vessel, allows the user to track the position of the distal end 27 which can be watched during translation of the needle 14 and catheter 12 under the skin. A disappearance of any of the area of the illuminated catheter 12 at the distal end 27, or a lessening in light discernable by the user as emanating from the distal end 27, is a clear signal that a blood vessel 18 has been punctured since the light emitted from the distal end 27 of the catheter 12 will significantly dim or disappear when positioned further into flesh and having to follow the noted third pathway to reach the eyes of the user.

Shown in FIGS. 1 and 2 is one mode of the light generating component 20 herein, formed in an annular ring like configuration which would engage on or in the introducer 16, in a position and shape adapted for operative engagement with the first or proximal end of the engaged catheter 12. The light generating component 20 is configured on a side facing catheter 12, such that light transmitted from the light generating component 20, communicates through the first or proximal end of the catheter 12, and in a fiber optic communication into and emanating from the sidewall defining the catheter 12, much like an LED illuminates a light rope or a fiber optic cable. In this mode, the light generating component 20 can be formed as a unitary structure with the first end of the catheter 12, or could be a separate component engageable in a sandwiched position between the first end of the catheter 12 and the introducer 16, or it may be formed in a unitary structure with the introducer 16.

In FIG. 3 shows another view of the device 10 of FIGS. 1-2 with a different view of the as-used positioning inserting a catheter 12. In FIG. 3 is depicted the light generating component 20 which is adapted to engage either the catheter 12 or the introducer 16, to achieve the sandwiched engagement between the catheter 12 and introducer 16.

Alternatively, the light generating component 20, can be configured to engage or be part of the rear end of the introducer 16 such as in FIG. 4. As shown this mode of the device 10 would include the introducer 16 provided for use in combination with the catheter 12 herein, and includes fiber optic channels 30 in or on the sidewall defining the flash chamber of the introducer, to communicate the light in the proper wavelength from the light generating component 20, the wall defining the catheter 12. As shown the catheter surrounds all but the distal end of the needle 14 which projects from the distal end 27 of the catheter 12.

In FIG. 5 is shown a front-positioned light generating component 20 which would preferably have LED generated light emitters emitting light at the desired wavelength and polarization or focused beam, to thereby communicate such light to and through the wall of the catheter 12 and radially from the catheter 12 when engaged over the needle 14.

FIGS. 6a-6d depict modes of formation of the catheter 12 wherein a lens or lenses 15 may be formed into the polymeric material forming the sidewall 13 of the catheter 12 to reflect and project light in a focused or directed fashion so as to render the light or the position of the emitted light on the catheter 12 easily seen through the flesh and skin of the patient during insertion thereof.

Such lenses 15 can be formed by annular grooves, multiple detents and angled cuts and grooves and the like formed into the sidewall 13 of either the catheter 12 or the introducer 16. The lenses 15 shown should not be limiting as any such lens which can be formed as would occur to those skilled in the art, to render the catheter 12 and positions of all or a portion thereof visibly discernable, by transmission of light 25 through the flesh and skin of the patient as described above. Also, the various angles and grooves and the like can be combined, or might be surfaced on one or both sides with a mirror coating that is bio-acceptable for use during the insertion procedure to provide a lens or lenses formed into or on the catheter 12 surfaces to render all or portions thereof discernable for location through the flesh and skin of the patient.

As can be discerned by those skilled in the art, there are numerous ways to generate the light using a light generating component 20 and communicate the light projecting therefrom to the proximal end of a catheter 12 which may be adapted in construction to absorb the communicated light and communicate such through and from the sidewall defining the catheter surrounding the needle 14. All such modes of light generation and communication to and from the catheter 12 as would occur to those skilled in the art are anticipated within the scope of this patent and the claims herein.

As noted, FIGS. 7a and 7b depicts a mode of a light generating component 20 using LEDs 21 engaged with an onboard power source such as a battery 29 employable as described above with the device 10 herein, but should not be considered limiting in any fashion as any light generating component 20 as would occur to those skilled in the art for use with the device 20 herein is considered included in the scope of this patent.

In FIG. 7a the LEDs 21 providing light for the light generating component 20 are formed in an annular array of LED's and would be in a circumferential size such that the sidewall 13 of the catheter 12 or of the introducer 16 depending on where the light generating component 20 is located, will project light down the respective sidewall mated to the light generating component 20.

In FIG. 7b is shown a sectional view of a light generating component 20 such as in FIG. 7a also showing the onboard electric power supply in the form of a battery 29 and internal circuitry 31 to communicate electric power to the LEDs 21. Also shown are a focusing lens 23 adjacent each LED 21 which is shaped to channel the light generated by the LEDs 21 into a sidewall 13 of either the catheter or flash chamber depending on the positioning of the light generating component 20 as described above in the different positions on the catheter 12, or in a sandwiched position between the catheter 12 and the introducer 16, or at the rear of the introducer 16.

Further, any of the different configurations and components can be employed with any other configuration or components shown and described herein. Additionally, while the present invention has been described herein with reference to particular embodiments thereof and steps in the method of production, a latitude of modifications, various changes and substitutions are intended in the foregoing disclosures, it will be appreciated that in some instance some features, or configurations, or steps in formation of the invention could be employed without al corresponding use of other features without departing from the scope of the invention as set forth in the following claims. All such changes, alternations and modifications as would occur to those skilled in the art are considered to be within the scope of this invention as broadly defined in the appended claims.

What is claimed is:

1. An illuminated catheterization apparatus, comprising:
a catheter having a proximal end and a distal end and having a sidewall communicating therebetween, said sidewall surrounding an axial passage through said catheter, wherein said passage is configured to communicate fluids from said proximal to said distal end;
said catheter adapted for engagement upon a needle projecting from a first end of an introducer with said proximal end adjacent said first end of said introducer and said needle communicating through said axial passage;
a light generating component in a position to communicate light projecting therefrom, into said sidewall of said catheter at said proximal end; and
said light illuminating said catheter and emanating from said sidewall, whereby said light emanating from said sidewall illuminates an insertion site for said catheter on a body of a patient, and communicates through flesh adjacent said insertion site upon an insertion of said catheter therein.

2. The illuminated catheterization apparatus of claim 1 wherein said position of said light generating component, is in a sandwiched engagement between said proximal end of said catheter and said first end of said introducer.

3. The illuminated catheterization apparatus of claim 1 wherein said position of said light generating component, is adjacent a rear end of said introducer opposite said first end.

4. The illuminated catheterization apparatus of claim 1 wherein at least one lens is formed into said sidewall of said catheter; and
said light emanating from said sidewall of said catheter also is projected from said at least one lens formed in said sidewall.

5. The illuminated catheterization apparatus of claim 2 wherein at least one lens is formed into said sidewall of said catheter; and
said light emanating from said sidewall of said catheter also is projected from said at least one lens formed in said sidewall.

6. The illuminated catheterization apparatus of claim 3 wherein at least one lens is formed into said sidewall of said catheter; and
said light emanating from said sidewall of said catheter also is projected from said at least one lens formed in said sidewall.

7. The illuminated catheterization apparatus of claim 4 wherein
said at least one lens is formed adjacent said distal end of said catheter; and
said light projected from said at least one lens through said flesh adjacent said insertion site provides a position locator for said distal end of said catheter.

8. The illuminated catheterization apparatus of claim 5 wherein
said at least one lens is formed adjacent said distal end of said catheter; and
said light projected from said at least one lens through said flesh adjacent said insertion site provides a position locator for said distal end of said catheter.

9. The illuminated catheterization apparatus of claim 6 wherein
said at least one lens is formed adjacent said distal end of said catheter; and
said light projected from said at least one lens through said flesh adjacent said insertion site provides a position locator for said distal end of said catheter.

10. The illuminated catheterization apparatus of claim 1 wherein said light generating component includes an LED for generating said light; and
a focusing lens adjacent said LED configured to focus all said light into said sidewall of said catheter.

11. The illuminated catheterization apparatus of claim 2 wherein said light generating component includes an LED for generating said light; and
  a focusing lens adjacent said LED configured to focus all said light into said sidewall of said catheter.

12. The illuminated catheterization apparatus of claim 5 wherein said light generating component includes an LED for generating said light; and
  a focusing lens adjacent said LED configured to focus all said light into said sidewall of said catheter.

13. The illuminated catheterization apparatus of claim 8 wherein said light generating component includes an LED for generating said light; and
  a focusing lens adjacent said LED configured to focus all said light into said sidewall of said catheter.

14. The illuminated catheterization apparatus of claim 1 wherein said light is at a wavelength between 650 to 1350 nm.

15. The illuminated catheterization apparatus of claim 1 wherein said light is at a wavelength between 700 to 900 nm.

16. The illuminated catheterization apparatus of claim 1 wherein said light generating component comprises an annular array of LEDs and an electric power supply, said light generating component being positioned distal of said introducer and proximal of said catheter.

17. The illuminated catheterization apparatus of claim 1 further comprising a plurality of lenses positioned along said catheter.

18. The illuminated catheterization apparatus of claim 17 wherein said plurality of lenses are formed by annular grooves, detents or angled cuts in said sidewall.

19. The illuminated catheterization apparatus of claim 18 wherein said plurality of lenses are surfaced with a mirror coating.

20. An illuminated catheterization apparatus, comprising:
  a catheter having a proximal end and a distal end and having a sidewall communicating therebetween, said sidewall surrounding an axial passage through said catheter, wherein said passage is configured to communicate fluids from said proximal to said distal end;
  said catheter adapted for engagement upon a needle projecting from a first end of an introducer with said proximal end adjacent said first end of said introducer and said needle communicating through said axial passage;
  an annular light generating component comprising at least one LED configured to generate light and communicate said light into said sidewall of said catheter at said proximal end, said annular light generating component forming a unitary structure with said catheter; and
  said light illuminating said catheter and emanating from said sidewall, whereby said light emanating from said sidewall illuminates an insertion site for said catheter on a body of a patient, and communicates through flesh adjacent said insertion site upon an insertion of said catheter therein.

* * * * *